United States Patent
Alferness (12)

(10) Patent No.: US 6,241,654 B1
(45) Date of Patent: Jun. 5, 2001

(54) CARDIAC REINFORCEMENT DEVICES AND METHODS

(75) Inventor: Clifton A. Alferness, Redmond, WA (US)

(73) Assignee: Acorn Cardiovasculr, Inc., St. Paul, MN (US)

( * ) Notice: Subject to any disclaimer, the term of this patent is extended or adjusted under 35 U.S.C. 154(b) by 0 days.

(21) Appl. No.: 09/348,697

(22) Filed: Jul. 7, 1999

(51) Int. Cl.[7] .................................................. A61F 2/00
(52) U.S. Cl. ................................................................ 600/37
(58) Field of Search ................................ 600/37, 16–18; 623/66, 1, 2, 11; 128/897–899; 606/151

(56) References Cited

U.S. PATENT DOCUMENTS

| | | |
|---|---|---|
| 3,983,863 | 10/1976 | Janke et al. . |
| 4,048,990 | 9/1977 | Goetz . |
| 4,403,604 | 9/1983 | Wilkinson et al. . |
| 4,428,375 | 1/1984 | Ellman . |

(List continued on next page.)

FOREIGN PATENT DOCUMENTS

| | | |
|---|---|---|
| 295 17 393 U1 | 3/1996 | (DE) . |
| 198 26 675 A1 | 3/1999 | (DE) . |
| 0 280 564 A2 | 8/1988 | (EP) . |
| 60-203250 | 10/1985 | (JP) . |
| 01 145066 | 6/1989 | (JP) . |
| 1009457 | 4/1983 | (RU) . |
| WO 98/29041 | 7/1998 | (WO) . |
| WO 98/58598 | 12/1998 | (WO) . |
| 98/58598 * | 12/1998 | (WO) .................................. 600/37 |

OTHER PUBLICATIONS

Capouya, E. et al., "Girdling Effect of Nonstimulated Cardiomyoplasty on Left Ventricular Function", *Society of Thoracic Surgeons*, pp. 867–871 )©1993).

Cohn, J., "The Management of Chronic Heart Failure", *The New England Journal of Medicine*, vol. 335, No. 7, pp. 490–498, (Aug. 15, 1996).

Guasp, F., "Una prótesis contentiva para el tratamiento de la miocardiopatia dilatada", *Revista Españñola de Cardiologia*, vol. 51, No. 7, pp. 521–528 (Jul. 1998).

Kass, D. et al., "Reverse Remodeling From Cardiomyoplasty in Human Heart Failure, External Constraint Versus Active Assist", *American Heart Association, Inc. Circulation*, vol. 91, No. 9, pp. 2314–2318 (May 1, 1995).

Levin, H. et al., "Reversal of Chronic Ventricular Dilation in Patients With End–Stage Cardiomyopathy by Prolonged Mechanical Unloading", *American Heart Association, Inc. Circulation*, vol. 91, No. 11, pp. 2717–2720 (Jun. 1, 1995).

(List continued on next page.)

*Primary Examiner*—Samuel G. Gilbert
(74) *Attorney, Agent, or Firm*—Merchant & Gould P.C.

(57) ABSTRACT

The present disclosure is directed to materials, devices, and methods for treatment of cardiac conditions including, for example, cardiomyopathy and valvular insufficiency. The devices and methods are directed to constraining expansion of the heart during diastole to a predetermined limit. In one embodiment, a material of the invention is a weave material that can be applied to the heart as a wrap of a two-dimensional sheet or shaped into a jacket. A cardiac reinforcement device of the invention can be applied to the heart to constrain cardiac expansion to a predetermined limit.

14 Claims, 8 Drawing Sheets

U.S. PATENT DOCUMENTS

| | | |
|---|---|---|
| 4,630,597 | 12/1986 | Kantrowitz et al. . |
| 4,690,134 | 9/1987 | Snyders . |
| 4,821,723 | 4/1989 | Baker, Jr. et al. . |
| 4,834,707 | 5/1989 | Evans . |
| 4,878,890 | 11/1989 | Bilweis . |
| 4,936,857 | 6/1990 | Kulik . |
| 4,957,477 | 9/1990 | Lundbäck . |
| 4,973,300 | 11/1990 | Wright . |
| 4,976,730 | 12/1990 | Kwan-Gett . |
| 5,057,117 | 10/1991 | Atweh . |
| 5,087,243 | 2/1992 | Avitall . |
| 5,131,905 | 7/1992 | Grooters . |
| 5,150,706 | 9/1992 | Cox et al. . |
| 5,186,711 | 2/1993 | Epstein . |
| 5,192,314 | 3/1993 | Daskalakis . |
| 5,256,132 | 10/1993 | Snyders . |
| 5,290,217 | 3/1994 | Campos . |
| 5,356,432 | 10/1994 | Rutkow et al. . |
| 5,383,840 | 1/1995 | Heilman et al. . |
| 5,385,156 | 1/1995 | Oliva . |
| 5,429,584 | 7/1995 | Chiu . |
| 5,507,779 | 4/1996 | Altman . |
| 5,524,633 | 6/1996 | Heaven et al. . |
| 5,603,337 | 2/1997 | Jarvik . |
| 5,647,380 | 7/1997 | Campbell et al. . |
| 5,702,343 | 12/1997 | Alferness . |
| 5,713,954 | 2/1998 | Rosenberg et al. . |
| 5,800,528 | 9/1998 | Lederman et al. . |
| 6,077,214 * | 6/2000 | Mortier et al. ............... 600/37 X |
| 6,085,754 * | 7/2000 | Alfreness et al. ............ 128/898 |

OTHER PUBLICATIONS

Oh, J. et al., "The Effects of Prosthetic Cardiac Binding and Adynamic Cardiomyoplasty in a Model of Dilated Cardiomyopathy", *The Journal of Thoracic and Cardiovascular Surgery*, vol. 116, No. 1, pp. 148–153 (Jul. 1998).

Paling, D., "Warp Knitting Technology", *Columbine Press*, 3 pages (Date Unknown).

Vaynblat, M. et al., "Cardiac Binding in Experimental Heart Failure", *Ann Thorac Surg*, vol. 64, No. 81, 11 pages, 64:81–5, (1997).

Abstract: Mikhail Vaynblat et al., Cardiac Binding in Experimental Heart Failure,: *Abstract* in Supplement to *Circulation* 92(8):1810 (Oct. 15, 1995).

* cited by examiner

CARDIAC REINFORCEMENT DEVICES AND METHODS

BACKGROUND OF THE INVENTION

Congestive heart disease is a progressive and debilitating illness. The disease is characterized by a progressive enlargement of the heart.

As the heart enlarges, the heart is performing an increasing amount of work in order to pump blood each heart beat. In time, the heart becomes so enlarged the heart cannot adequately supply blood. An afflicted patient is fatigued, unable to perform even simple exerting tasks and experiences pain and discomfort. Further, as the heart enlarges, the internal heart valves cannot adequately close. This impairs the function of the valves and further reduces the heart's ability to supply blood.

Causes of congestive heart disease are not fully known. In certain instances, congestive heart disease may result from viral infections. In such cases, the heart may enlarge to such an extent that the adverse consequences of heart enlargement continue after the viral infection has passed and the disease continues its progressively debilitating course.

Patients suffering from congestive heart disease are commonly grouped into four classes (i.e., Classes I, II, III and IV) according to the New York Heart Association (NYHA). In the early stages (e.g., Classes I and II), drug therapy is the commonly prescribed treatment. Drug therapy treats the symptoms of the disease and may slow the progression of the disease. Importantly, there is no cure for congestive heart disease. Even with drug therapy, the disease will progress. Further, the drugs may have adverse side effects.

Presently, the only permanent treatment for congestive heart disease is heart transplant. To qualify, a patient must be in the later stage of the disease (e.g., Classes III and IV with Class IV patients given priority for transplant). Such patients are extremely sick individuals. Class III patients have marked physical activity limitations and Class IV patients are symptomatic even at rest.

Due to the absence of effective intermediate treatment between drug therapy and heart transplant, Class III and IV patients will have suffered terribly before qualifying for heart transplant. Further, after such suffering, the available treatment is unsatisfactory. Heart transplant procedures are very risky, extremely invasive and expensive and only shortly extend a patient's life. For example, prior to transplant, a Class IV patient may have a life expectancy of 6 months to one year. Heart transplant may improve the expectancy to about five years.

Unfortunately, not enough hearts are available for transplant to meet the needs of congestive heart disease patients. In the United States, in excess of 35,000 transplant candidates compete for only about 2,000 transplants per year. A transplant waiting list is about 8–12 months long on average and frequently a patient may have to wait about 1 to 2 years for a donor heart. While the availability of donor hearts has historically increased, the rate of increase is slowing dramatically. Even if the risks and expense of heart transplant could be tolerated, this treatment option is becoming increasingly unavailable. Further, many patients do not qualify for heart transplant for failure to meet any one of a number of qualifying criteria.

Congestive heart failure has an enormous societal impact. In the United States alone, about five million people suffer from the disease (Classes I through IV combined). Alarmingly, congestive heart failure is one of the most rapidly accelerating diseases (about 400,000 new patients in the United States each year). Economic costs of the disease have been estimated at $38 billion annually.

Not surprising, substantial effort has been made to find alternative treatments for congestive heart disease. Recently, a new surgical procedure has been developed. Referred to as the Batista procedure, the surgical technique includes dissecting and removing portions of the heart in order to reduce heart volume. This is a radical new and experimental procedure subject to substantial controversy. Furthermore, the procedure is highly invasive, risky, and expensive and commonly includes other expensive procedures (such as a concurrent heart valve replacement). Also, the treatment is limited to Class IV patients and, accordingly, provides no hope to patients facing ineffective drug treatment prior to Class IV. Finally, if the procedure fails, emergency heart transplant is the only available option.

Clearly, there is a need for alternative treatments applicable to both early and later stages of the disease to either stop the progressive nature of the disease or more drastically slow the progressive nature of congestive heart disease. Unfortunately, currently developed options are experimental, costly, and problematic.

Cardiomyoplasty is a recently developed treatment for earlier stage congestive heart disease (e.g., as early as Class III dilated cardiomyopathy). In this procedure, the latissimus dorsi muscle (taken from the patient's shoulder) is wrapped around the heart and chronically paced synchronously with ventricular systole. Pacing of the muscle results in muscle contraction to assist the contraction of the heart during systole.

While cardiomyoplasty has resulted in symptomatic improvement, the nature of the improvement is not understood. For example, one study has suggested the benefits of cardiomyoplasty are derived less from active systolic assist than from remodeling, perhaps because of an external elastic constraint. The study suggests an elastic constraint (i.e., a non-stimulated muscle wrap or an artificial elastic sock placed around the heart) could provide similar benefits. Kass et al., *Reverse Remodeling From Cardiomyoplasty In Human Heart Failure: External Constraint Versus Active Assist*, 91 *Circulation* 2314–2318 (1995).

Even though cardiomyoplasty has demonstrated symptomatic improvement, studies suggest the procedure only minimally improves cardiac performance. The procedure is highly invasive requiring harvesting a patient's muscle and an open chest approach (i.e., sternotomy) to access the heart. Furthermore, the procedure is expensive—especially those using a paced muscle. Such procedures require costly pacemakers. The cardiomyoplasty procedure is complicated. For example, it is difficult to adequately wrap the muscle around the heart with a satisfactory fit. Also, if adequate blood flow is not maintained to the wrapped muscle, the muscle may necrose. The muscle may stretch after wrapping reducing its constraining benefits and is generally not susceptible to post-operative adjustment. Finally, the muscle may fibrose and adhere to the heart causing undesirable constraint on the contraction of the heart during systole.

In addition to cardiomyoplasty, mechanical assist devices have been developed as intermediate procedures for treating congestive heart disease. Such devices include left ventricular assist devices ("LVAD") and total artificial hearts ("TAH"). An LVAD includes a mechanical pump for urging blood flow from the left ventricle and into the aorta. An example of such is shown in U.S. Pat. No. 4,995,857 to Arnold dated Feb. 26, 1991. LVAD surgeries are still in U.S.

clinical trials and not generally available. Such surgeries are expensive. The devices are at risk of mechanical failure and frequently require external power supplies. TAH devices, such as the celebrated Jarvik heart, are used as temporary measures while a patient awaits a donor heart for transplant.

Other attempts at cardiac assist devices are found in U.S. Pat. No. 4,957,477 to Lundbäck dated Sep. 18, 1990, U.S. Pat. No. 5,131,905 to Grooters dated Jul. 21, 1992 and U.S. Pat. No. 5,256,132 to Snyders dated Oct. 26, 1993. Both of the Grooters and Snyders patents teach cardiac assist devices which pump fluid into chambers opposing the heart to assist systolic contractions of the heart. The Lundbäck patent teaches a double-walled jacket surrounding the heart. A fluid fills a chamber between the walls of the jacket. The inner wall is positioned against the heart and is pliable to move with the heart. Movement of the heart during beating displaces fluid within the jacket chamber.

Commonly assigned U.S. Pat. No. 5,702,343 to Alferness dated Dec. 30, 1997 teaches a jacket to constrain cardiac expansion during diastole. The disclosures of each of the patents and publications cited within the present disclosure are incorporated herein by reference. The present invention pertains to improvements to the invention disclosed in the '343 patent.

SUMMARY OF THE INVENTION

The present invention is directed to weave materials, devices, and methods for reinforcement of a heart. According to the invention, a weave material comprises a plurality of cells and can be configured to be applied to a heart. The material of the invention can be applied to a heart in a two-dimensional sheet form or configured into the shape of a jacket to form a cardiac reinforcement device.

In one embodiment, a cardiac reinforcement device comprises a jacket having a plurality of circumferential rows of cells approximately perpendicular to a longitudinal axis of the jacket. Each circumferential row of the jacket comprises an equal number of cells. Each cell has a cell area, and the cell area may vary from one circumferential row to another but is approximately constant for cells in the same circumferential row.

In another embodiment, the cell area of cells in a selected circumferential row is directly correlated with a cross-sectional circumferential dimension of a heart that is surrounded by the selected circumferential row of cells.

In other embodiments, methods of constraining cardiac expansion using the material of the invention are described. In one such method, a jacket of the invention can be applied over a plurality of cross-sectional circumferential dimensions of the heart from the apex to the base and each cross-sectional circumferential dimension is surrounded by a circumferential row of cells having a cell area correlated with the cross-sectional circumferential dimension.

DETAILED DESCRIPTION OF THE PREFERRED EMBODIMENT

The present invention provides materials, devices, and methods for treatment of cardiac conditions such as cardiomyopathy and valvular insufficiency. Generally, the invention is directed to constraining expansion of the heart during diastole to a predetermined limit. Specifically, the invention provides a weave material, a device incorporating the material, and methods for making and using the material and device.

The weave material of the invention is particularly advantageous for treatment of certain cardiac conditions. In a preferred embodiment, when the material is configured into a jacket for constraining expansion of the heart, the unique material and methods of the invention provide for symmetrical cardiac constraint. As used herein, "symmetrical cardiac constraint" (SCC) means that the resistance force applied to the surface area of the heart by the jacket during constraint is distributed symmetrically over the surface of the heart covered by the jacket. Not only does symmetrical cardiac constraint provide symmetrical support to the myocardium during diastole, but also, it reduces the likelihood of compression injuries to the heart surface during constraint.

Figure 1:
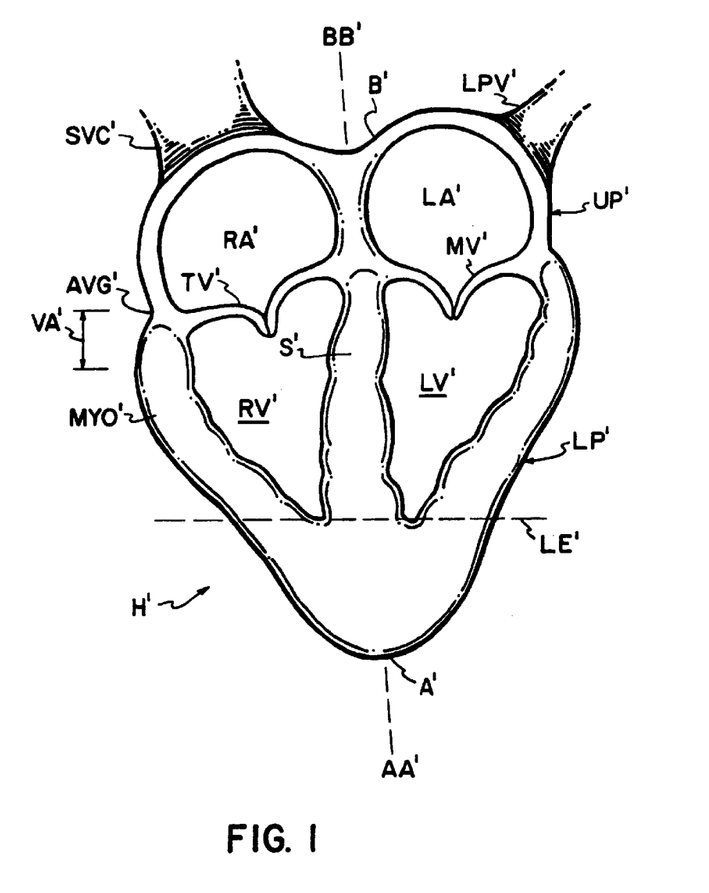
FIG. 1 is a schematic cross-sectional view of a normal, healthy human heart shown during systole.
Figure 1A:
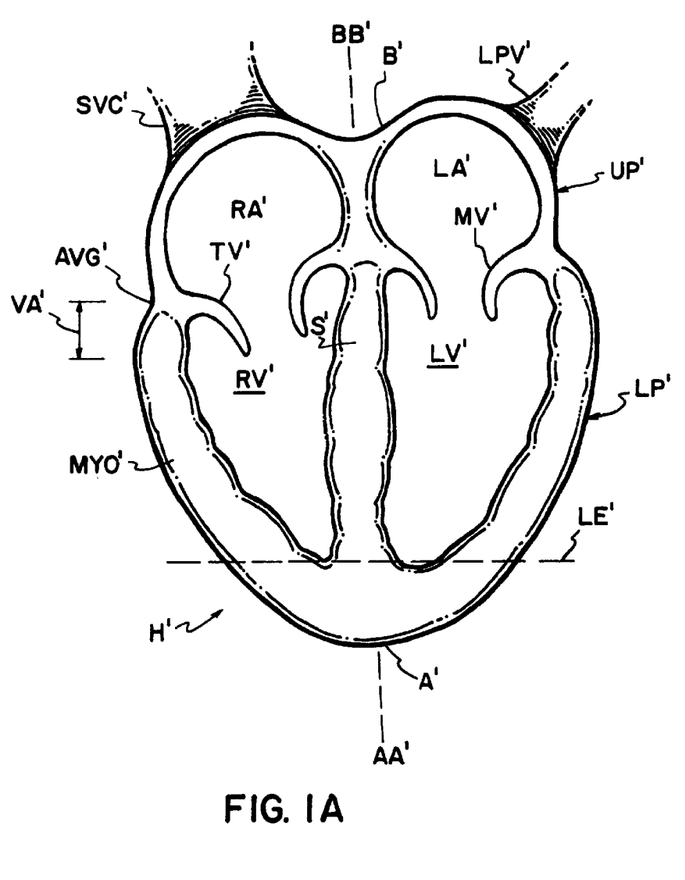
FIG. 1A is the view of FIG. 1 showing the heart during diastole.

With initial reference to FIGS. 1 and 1A, a normal, healthy human heart H' is schematically shown in cross-section and will now be described in order to facilitate an understanding of the present invention. In FIG. 1, the heart H' is shown during systole (i.e., high left ventricular pressure). In FIG. 1A, the heart H' is shown during diastole (i.e., low left ventricular pressure).

The heart H' is a muscle having an outer wall or myocardium MYO' and an internal wall or septum S'. The myocardium MYO' and septum S' define four internal heart chambers including a right atrium RA', a left atrium LA', a right ventricle RV' and a left ventricle LV'. The heart H' has a length measured along a longitudinal axis BB'–AA' from an upper end or base end B' to a lower end or apex end A'.

The right and left atria RA', LA' reside in an upper portion UP' of the heart H' adjacent the base B'. The right and left ventricles RV', LV' reside in a lower portion LP' of the heart H' adjacent the apex A'. The ventricles RV', LV' terminate at ventricular lower extremities LE' adjacent the apex A' and spaced therefrom by the thickness of the myocardium MYO'.

Due to the compound curves of the upper and lower portions UP', LP', the upper and lower portions UP', LP' meet at a circumferential groove commonly referred to as the A–V groove AVG'. Extending away from the upper portion UP' are a plurality of major blood vessels communicating with the chambers RA', RV', LA', LV'. For ease of illustration, only the superior vena cava SVC' and a left pulmonary vein LPV' are shown as being representative.

The heart H' contains valves to regulate blood flow between the chambers RA', RV', LA', LV' and between the chambers and the major vessels (e.g., the superior vena cava SVC' and a left pulmonary vein LPV'). For ease of illustration, not all of such valves are shown. Instead, only the tricuspid valve TV' between the right atrium RA' and right ventricle RV' and the mitral valve MV' between the left atrium LA' and left ventricle LV' are shown as being representative.

The valves are secured, in part, to the myocardium MYO' in a region of the lower portion LP' adjacent the A–V groove AVG' and referred to as the valvular annulus VA'. The valves TV' and MV' open and close through the beating cycle of the heart H.

FIGS. 1 and 1A show a normal, healthy heart H' during systole and diastole, respectively. During systole (FIG. 1), the myocardium MYO' is contracting and the heart assumes a shape including a generally conical lower portion LP'. During diastole (FIG. 1A), the heart H' is expanding and the conical shape of the lower portion LP' bulges radially outwardly (relative to axis BB'–AA').

The motion of the heart H' and the variation in the shape of the heart H' during contraction and expansion is complex. The amount of motion varies considerably throughout the heart H'. The motion includes a component which is parallel to the axis BB'–AA'(conveniently referred to as longitudinal expansion or contraction). The motion also includes a component perpendicular to the axis BB'–AA' (conveniently referred to as radial circumferential expansion or contraction).

Having described a healthy heart H' during systole (FIG. 1) and diastole (FIG. 1A), comparison can now be made with a heart deformed by congestive heart disease. Such a heart H is shown in systole in FIG. 2 and in diastole in FIG. 2A. All elements of diseased heart H are labeled identically with similar elements of healthy heart H' except only for the omission of the apostrophe in order to distinguish diseased heart H from healthy heart H'.

Figure 2:
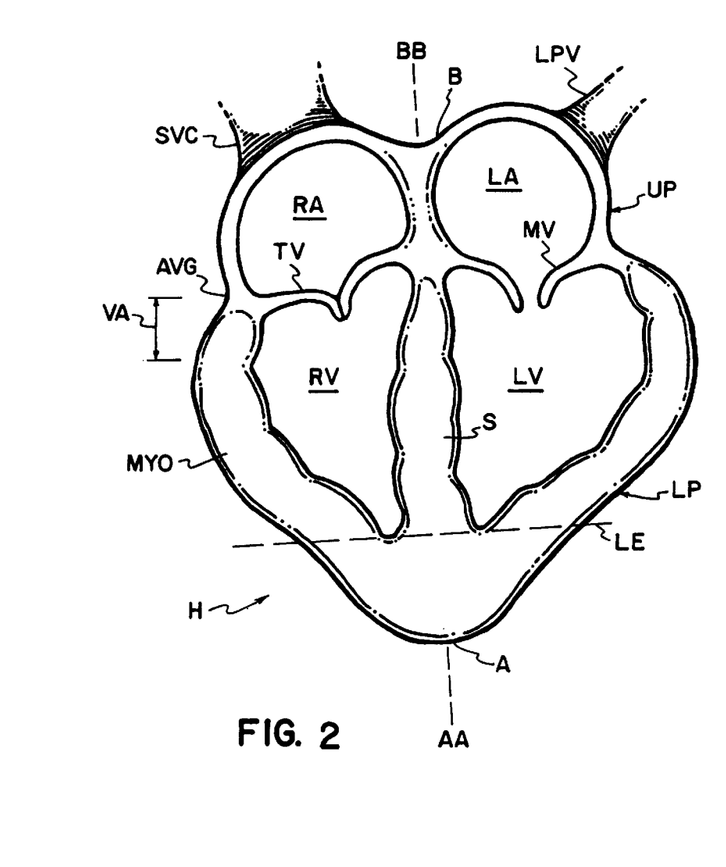
FIG. 2 is a schematic cross-sectional view of a diseased human heart shown during systole.

Comparing FIGS. 1 and 2 (showing hearts H' and H during systole), the lower portion LP of the diseased heart H has lost the tapered conical shape of the lower portion LP' of the healthy heart H'. Instead, the lower portion LP of the diseased heart H bulges outwardly between the apex A and the A–V groove AVG. So deformed, the diseased heart H during systole (FIG. 2) resembles the healthy heart H' during diastole (FIG. 1A). During diastole (FIG. 2A), the deformation is even more extreme.

Figure 2A:
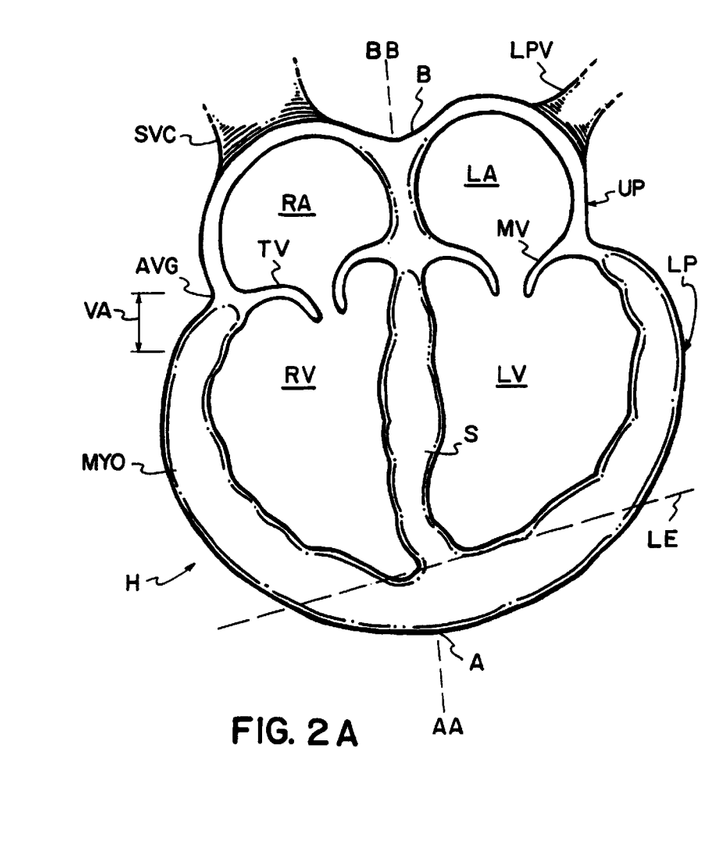
FIG. 2A is the view of FIG. 2 showing the heart during diastole.

As a diseased heart H enlarges from the representation of FIGS. 1 and 1A to that of FIGS. 2 and 2A, the heart H becomes a progressively inefficient pump. Therefore, the heart H requires more energy to pump the same amount of blood. Continued progression of the disease results in the heart H being unable to supply adequate blood to the patient's body and the patient becomes symptomatic of cardiac insufficiency.

For ease of illustration, the progression of congestive heart disease has been illustrated and described with reference to a progressive enlargement of the lower portion LP of the heart H. While such enlargement of the lower portion LP is most common and troublesome, enlargement of the upper portion UP may also occur.

In addition to cardiac insufficiency, the enlargement of the heart H can lead to valvular disorders. As the circumference of the valvular annulus VA increases, the leaflets of the valves TV and MV may spread apart. After a certain amount of enlargement, the spreading may be so severe the leaflets cannot completely close (as illustrated by the mitral valve MV in FIG. 2A). Incomplete closure results in valvular regurgitation contributing to an additional degradation in cardiac performance. While circumferential enlargement of the valvular annulus VA may contribute to valvular dysfunction as described, the separation of the valve leaflets is most commonly attributed to deformation of the geometry of the heart H. This is best described with reference to FIGS. 1B and 2B.

Figure 1B:
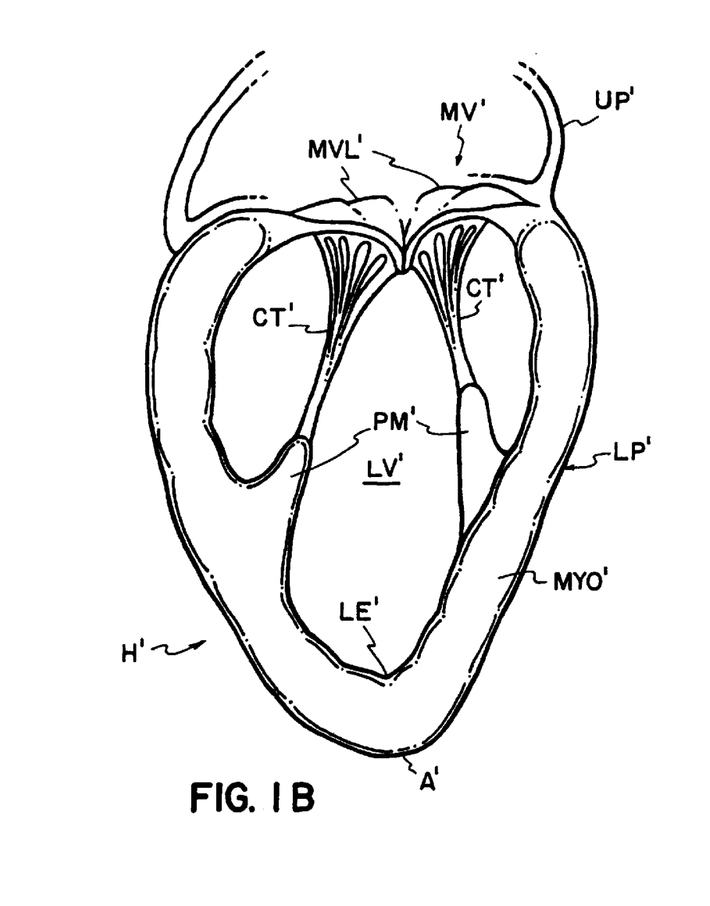
FIG. 1B is a view of a left ventricle of a healthy heart as viewed from a septum and showing a mitral valve.
Figure 2B:
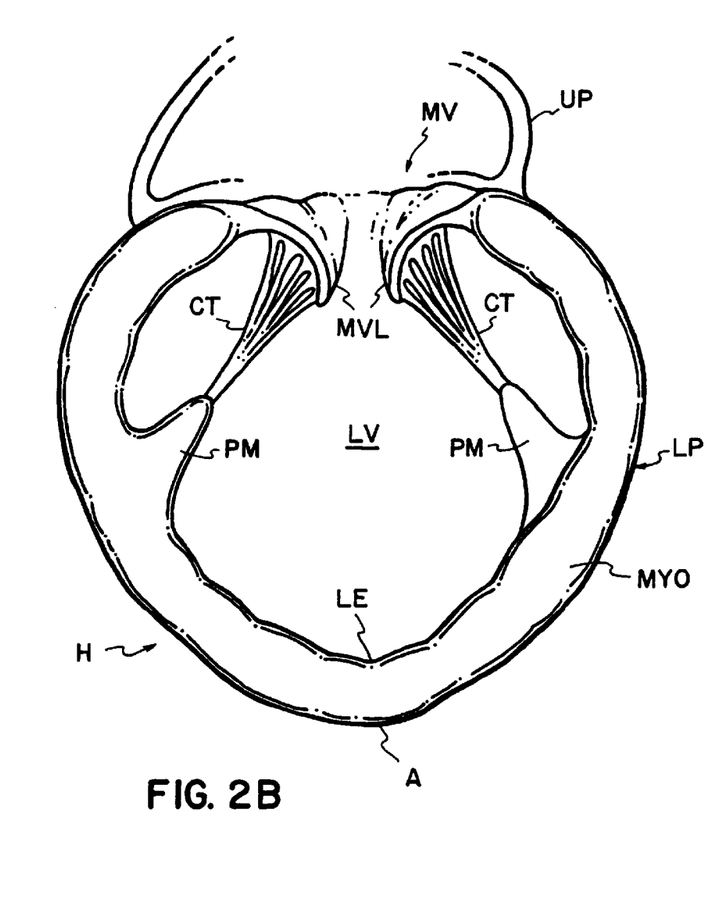
FIG. 2B is the view of FIG. 1B showing a diseased heart.

FIGS. 1B and 2B show a healthy and diseased heart, respectively, left ventricle LV', LV during systole as viewed from the septum (not shown in FIGS. 1B and 2B). In a healthy heart H', the leaflets MVL' of the mitral valve MV' are urged closed by left ventricular pressure. The papillary muscles PM', PM are connected to the heart wall MYO', MYO, near the lower ventricular extremities LE', LE. The papillary muscles PM', PM pull on the leaflets MVL', MVL via connecting chordae tendineae CT', CT. Pull of the leaflets by the papillary muscles functions to prevent valve leakage in the normal heart by holding the valve leaflets in a closed position during systole. In the significantly diseased heart H, the leaflets of the mitral valve may not close sufficiently to prevent regurgitation of blood from the ventricle LV to the atrium during systole.

As shown in FIG. 1B, the geometry of the healthy heart H' is such that the myocardium MYO', papillary muscles PM' and chordae tendineae CT' cooperate to permit the mitral valve MV' to fully close. However, when the myocardium MYO bulges outwardly in the diseased heart H (FIG. 2B), the bulging results in displacement of the papillary muscles PM. This displacement acts to pull the leaflets MVL to a displaced position such that the mitral valve cannot fully close.

Having described the characteristics and problems with congestive heart disease, the present invention, including a novel material, a cardiac reinforcement device made from the material by forming a jacket, and methods for cardiac treatment will now be described.

A material according to the invention is a weave material. As used herein, a "weave material" includes knits, meshes, and other materials comprised of single or multi-filament strands that are interlaced at the intersection of any two strands of material to form a cell. Generally, the weave material of the invention comprises a plurality of cells defined by strands of a biocompatible material. As used herein, the term "cell" means an open area bordered by the strands of the material. The cells can be of any shape, including, for example, circular, oval, rectangular, square, diamond, hexagonal, etc.

The weave material of the invention is preferably made from a biomedical material. As used herein, a "biomedical material" is a weave material which is physiologically inert to minimize an immune reaction or other excessive inflammatory response. For instance, suitable biomedical materials include polypropylene, polyester, silicone rubber, and polytetrafluoroethylene, and expanded polytetrafluoroethylene. Preferably, the biomedical material is polyester. While all materials expand at least a small amount, the weave material is preferably formed of a material with a high modulus of elasticity. Thus, in response to the low pressures in the heart H during diastole, the weave material is non-elastic. Yet the biomedical material preferably is sufficiently flexible to move with the expansion and contraction of the heart without impairing systolic function. Furthermore, although the fibers are relatively inelastic, the weave pattern gives the material some compliance such that the material will expand a desirable distance and then resist further expansion. Additionally, an anti-fibrosis lining can be placed between the heart and the cardiac reinforcement device of the present invention. The fibers may be coated with a material to lessen or prevent fibrostic response, such as, for example, PTFE.

Figure 3:
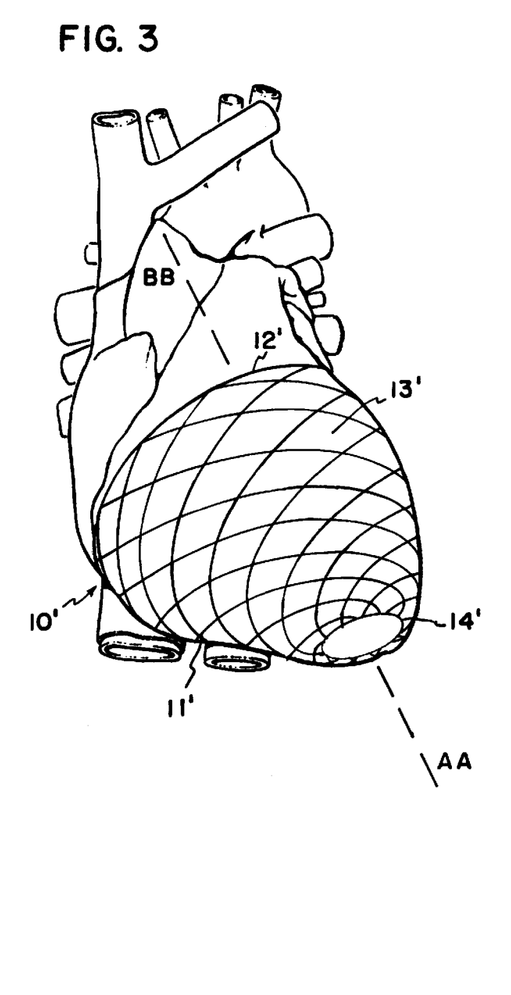
FIG. 3 is a perspective view of one embodiment of a cardiac reinforcement device according to the present invention applied to a heart.

FIG. 3 illustrates one embodiment of a weave material according to the invention when applied over the surface of the heart. According to this embodiment, the weave material is configured as a reinforcement device 10' comprising a jacket 11' with a base end 12' and an apex end 14'. The cells 13' will be fully discussed below.

Figure 4:
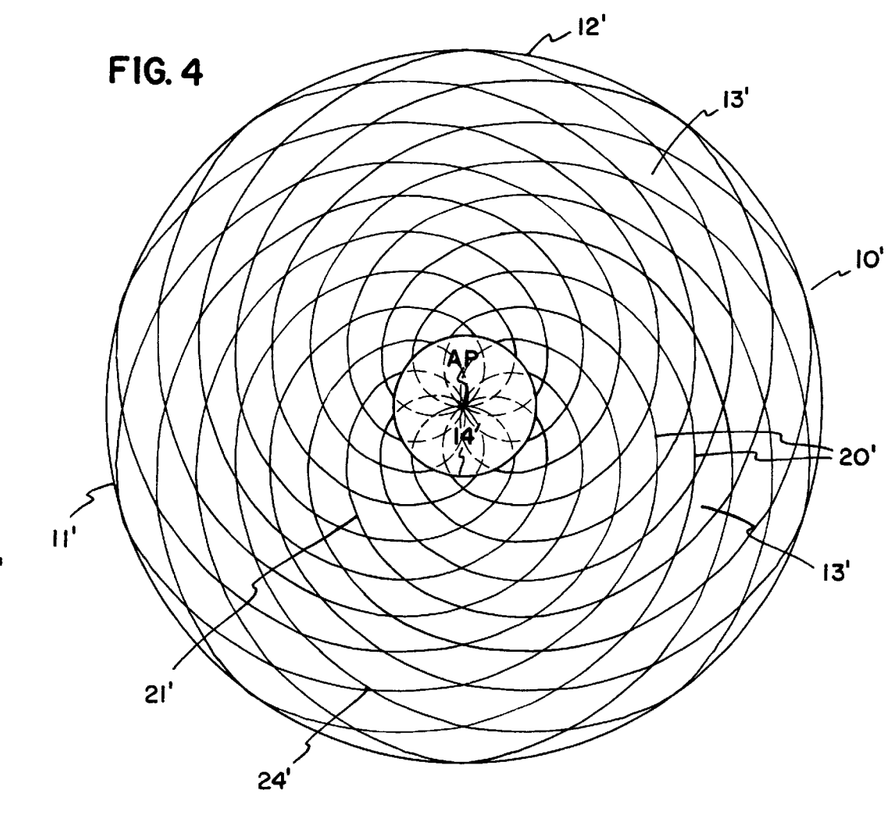
FIG. 4 is a view of the apical end of an embodiment of a cardiac reinforcement device analogous to the cardiac reinforcement device of FIG. 3.

FIG. 4 illustrates a view of the apical end 14' of a cardiac reinforcement device 10' having a jacket 11' analogous to the cardiac reinforcement device 10' of FIG. 3. According to this embodiment, the weave material includes intersecting strands of the biocompatible material which spiral in opposite directions from a common point. The cells 13' of the weave material are formed by the intersection of a first set of strands 20' spiraling in a clockwise direction outward from a common originating point AP at the apex end 14' and a second set of strands 21' spiraling in a counterclockwise direction outward from the common originating point AP at the apex end 14'. A similar pattern also arises if the spirals emanate from a common point at the base end of the jacket. The common point AP need not be physically present on the jacket 11' if the apex end of the jacket and the base end of the jacket are open as shown in FIG. 3. Thus, the common originating point AP is a reference point from which the strand spirals emanate such that if the revolution of each spiral were traced to a source point at the apex end 14' of the jacket, all spirals would intersect at point AP.

Figure 5:
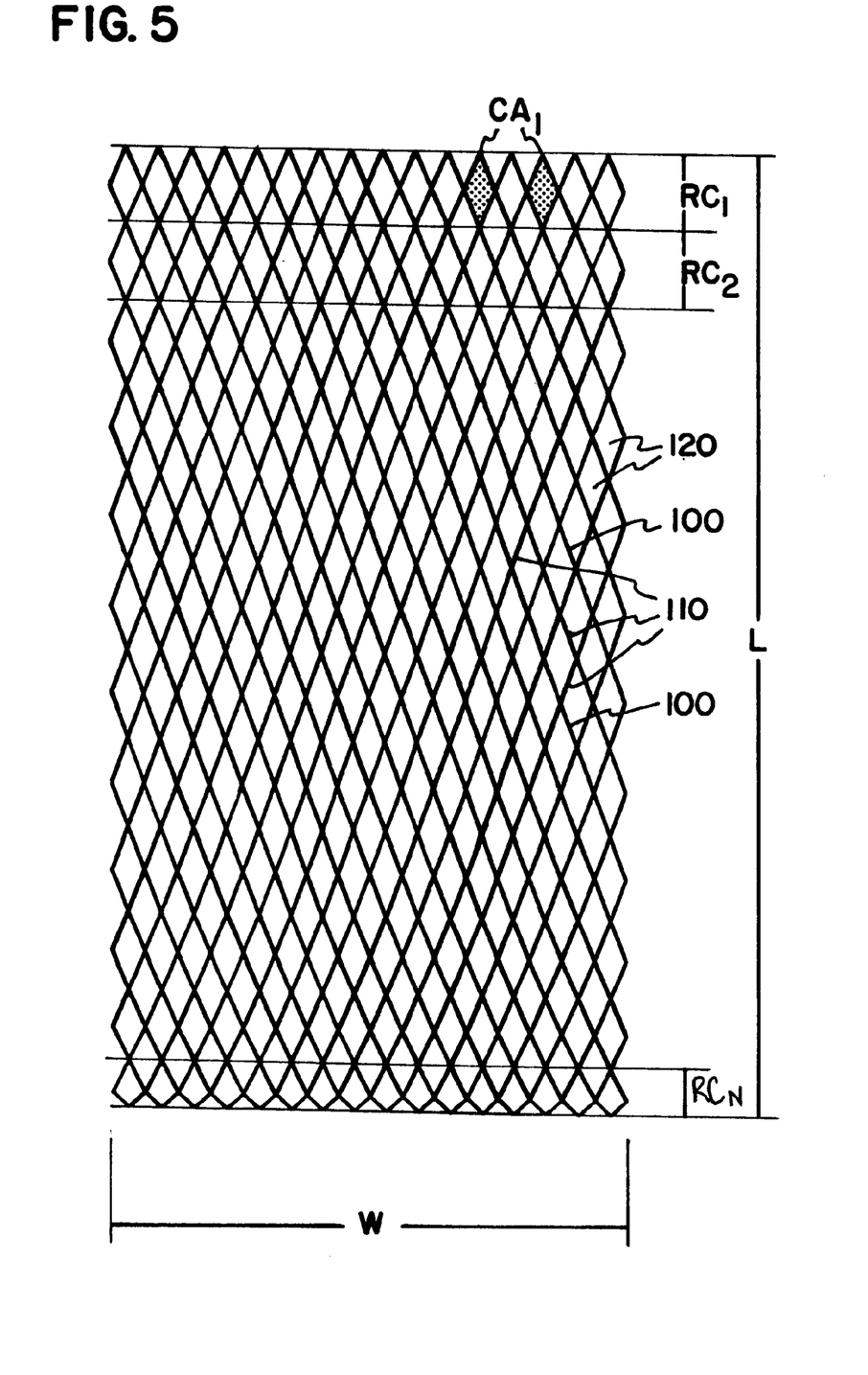
FIG. 5 is a plan view of one embodiment of a material according to the invention.

Referring now to FIG. 5, one embodiment of the weave material is illustrated in a two-dimensional, relaxed form. "Two-dimensional" as used herein refers to the weave material comprising a first dimension or a length L and a second dimension or width W. It will be appreciated that the weave material includes a third dimension comprising the thickness of the weave material. "Relaxed" as used herein refers to the weave material laying flat without any force being applied to the material.

As illustrated in FIG. 5, the weave material comprises a first set of strands 100 which intersect with a second set of strands 110 to form cells 120. In one embodiment, cells 120 can be arranged relative to a first linear dimension L and a second linear dimension W. According to the illustrated embodiment, rows of cells 120 may be arranged approximately parallel to the second dimension W. In FIG. 5, these rows are designated as $RC_1$, $RC_2$, ... $RC_N$. The number of cells 120 in any row is the same as the number of cells in any other row. For example, if row $RC_1$ has X cells, then all rows $RC_2$, ... $RC_N$ also each have X cells as well. The number of cells in a row can be determined by the total number of strands desired (i.e., strand density).

Each cell in a row also has a cell area CA. For any cell in a selected row, the cell area is approximately the same as the cell area of any other cell in that selected row. For example, if a cell $RC_1$ has area $CA_1$, then all cells in $RC_1$, have cell area of approximately $CA_1$. However, unlike the number of cells in a row, the cell area CA can vary from row to row, such as, for example, $RC_1$, to another, such as, for example, $RC_2$ or $RC_N$. For instance, if the cells in row $RC_1$ have area $CA_1$, the cells in row $RC_2$ need not have an area of $CA_1$.

According to the invention, when applied to the surface of a heart, the cell area CA is greater for a row of cells surrounding a large cross-sectional circumferential dimension of the heart than for a row of cells surrounding a smaller cross-sectional circumferential dimension of the heart. A "cross-sectional circumferential dimension" of the heart is the length of the perimeter around any cross-section of the heart taken in a plane that is perpendicular to the longitudinal axis of the heart.

Figure 6:
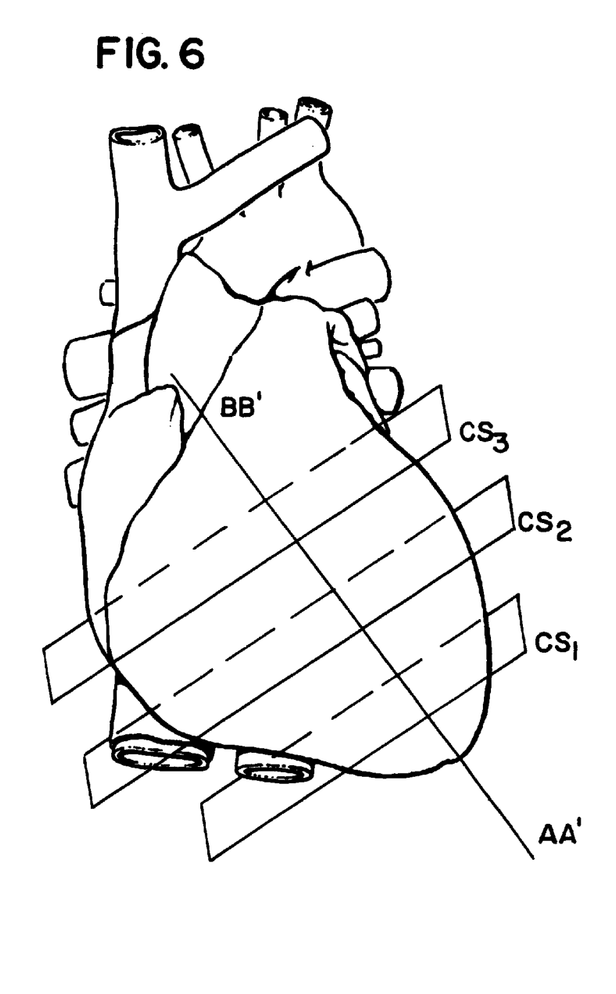
FIG. 6 illustrates cross-sectional planes of a heart which are perpendicular to the longitudinal axis of the heart BB'–AA'.
Figure 6A:
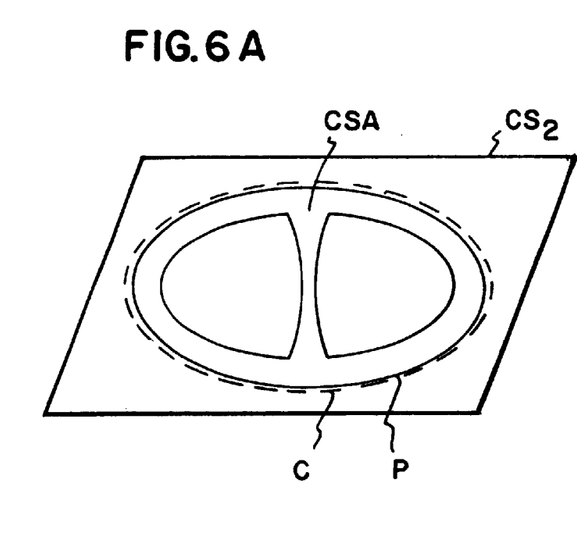
FIG. 6A is a schematic view of the area of the heart within a cross-sectional plane of FIG. 6.

For example, referring to FIG. 6, cross-sectional planes $CS_1$, $CS_2$, $CS_3$ are shown perpendicular to the longitudinal axis of the heart BB'–AA'. A schematic view of the area of the heart within cross-sectional plane $CS_2$ is shown in FIG. 6A. Cross-sectional plane $CS_2$ is used as an example for determining a cross-sectional circumferential dimension of a cross-sectional area of the heart within any cross-sectional plane. To determine the cross-sectional circumferential dimension, the perimeter P around the cross-sectional area CSA of the heart within cross-sectional plane $CS_2$ is measured. In other words, the length of the perimeter is equal to the circumference C. Thus, the circumference C of the cross-sectional area CSA of the heart within a cross-sectional plane is the cross-sectional circumferential dimension.

The depiction of three cross-sectional planes in FIG. 6 is for illustration purposes. In use, a plurality of cross-sectional circumferential dimensions is determined. Typically, a cross-sectional circumferential dimension will be determined for each row of cells. The cross-sectional circumferential dimension can be determined using, for example, standard imaging methods including, for example, MRI or CT scans.

In a preferred embodiment, the cell area CA of cells in a particular row directly correlates with a cross-sectional circumferential dimension of the heart that the row of cells surrounds relative to other cross-sectional circumferential dimensions. That is, the greater the cross-sectional circumferential dimension, the greater the area of the cells in the row of cells directly overlying that cross-sectional circumferential dimension. By "correlating" cell area with cross-sectional circumferential dimension of the heart, the cell area is determined as a function of the cross-sectional circumferential dimension of the heart. The cell area is determined so that when the weave material is applied to the heart or is shaped into a jacket and applied to the heart, each cell can widen sufficiently to provide desirable cardiac constraint. Thus, the cell area will be smaller for cells in a row applied over a region of the heart that has a smaller cross-sectional circumferential dimension than the cell area of cells in a row applied over a region of the heart having a larger cross-sectional circumferential dimension. The appropriate maximum cell area may be, for example, 1 to 100 $mm^2$, typically 16 to 85 $mm^2$.

Although the cell area varies with the cross-sectional circumferential dimension of the heart over which the row of cells is applied, the total number of cells in any given row is the same as the number of cells in any other row. Because the number of cells in any row is the same, the density of cells changes depending on the cross-sectional circumferential dimension. "Density," as used herein, refers to the number of cells in a row per cross-sectional circumferential dimension that corresponds to that row of the weave material. When the weave material is applied to the heart, the density of cells (i.e., number of cells/perimeter length) is greater for smaller cross-sectional circumferential dimensions than for larger cross-sectional circumferential dimensions.

The number of circumferential cross-sectional dimensions necessary to provide the advantages of a weave material according to the present invention is at least two. For example, a weave material can be prepared with cells having cell areas that correlate to a first circumferential cross-sectional dimension of the widest circumferential dimension of the heart and to a second circumferential cross-sectional dimension at a region between the widest dimension and the apex of the heart. Preferably, at least three circumferential cross-sectional dimensions are determined. In such an embodiment, for example, a weave material can be prepared with cells having cell areas that correlate to the first two cross-sectional circumferential dimensions which can be as defined above and to a third dimension which may be determined for a circumferential dimension between the first two cross-sectional circumferential dimensions of the heart. More preferably, a weave material can be prepared with cells having cell areas that correlate to more than three circumferential cross-sectional dimensions. Additional rows of cells may be provided that correlate with incremental cross-sectional circumferences between and above and below the cells that correspond to the three main circumferences described above.

A weave material according to the invention can be applied to the heart in a two-dimensional sheet form and shaped around the heart. When applied to the heart, the cells of a row are applied to the heart approximately along a circumferential plane of the heart having a circumferential dimension that corresponds with the cell area of the cells in that row.

In an alternative embodiment, before application to the heart the material can be configured into the shape of a jacket to form a cardiac reinforcement device. A jacket of the invention may be formed from a two-dimensional sheet of weave material by, for example, attaching all rows by joining a first cell in a selected row to a last cell in that selected row and conforming the weave material to the general shape of the heart to which it is applied.

With reference now to FIGS. 7, 7A, 8, and 8A, a device of the present invention is shown as the jacket 11 or 11' of a biologically compatible material. The difference between jackets 11 (FIGS. 7 and 7A) and 11' (FIGS. 8 and 8A) is that jacket 11' has an open apical end 14'. In both embodiments, the jackets 11 and 11', have base ends 12, 12' open. The jackets have a longitudinal axis JB–JA, JB'–JA' from the base end 12, 12' to the apex end 14, 14'. The jackets 11, 11' define an internal volume 16, 16' which is completely enclosed but for the open ends, 12, 12', and 14'.

Figure 7:
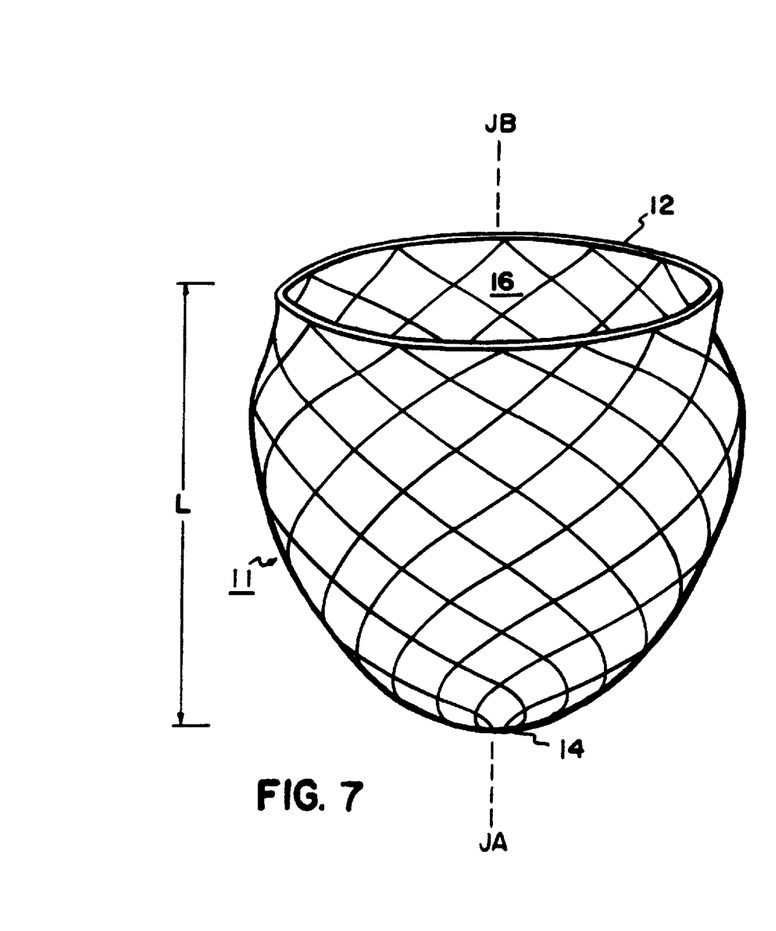
FIG. 7 is a perspective view of a third embodiment of a cardiac reinforcement device according to the invention.
Figure 7A:
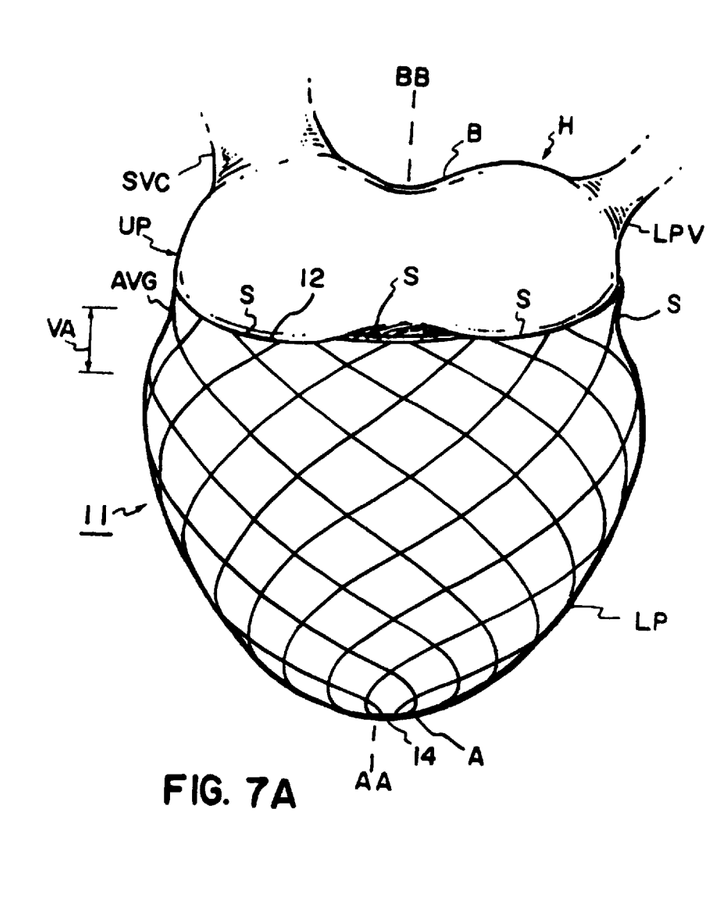
FIG. 7A illustrates a diseased heart in diastole with the device of FIG. 7 applied to the heart.
Figure 8:
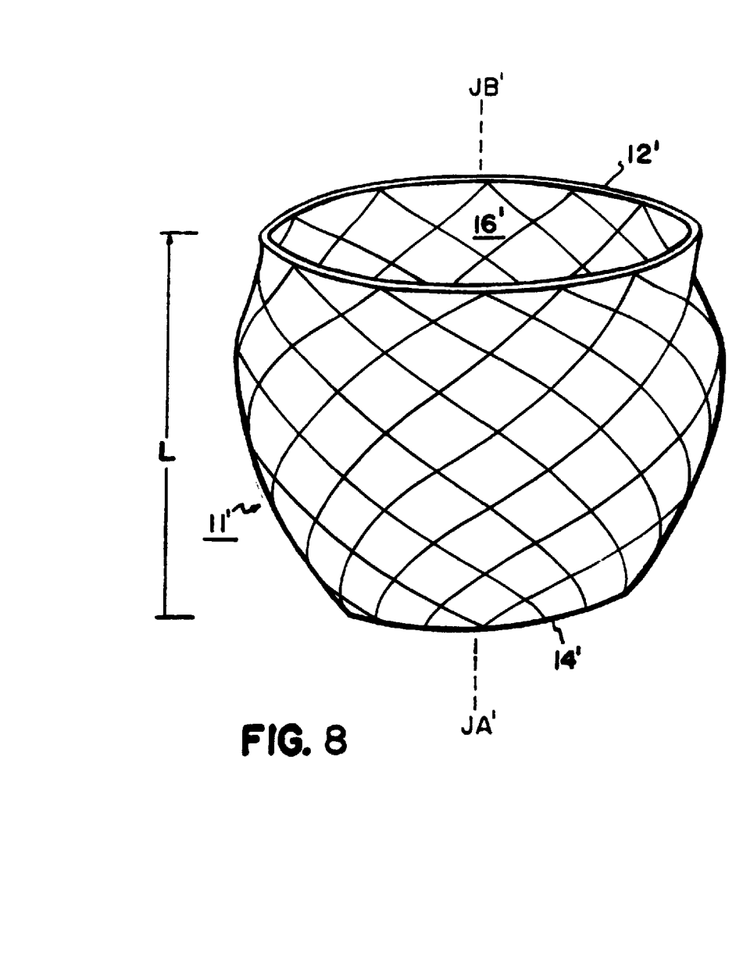
FIG. 8 is a perspective view of a fourth embodiment of a cardiac reinforcement device according to the invention.

For simplicity, the following discussion is directed to the jacket 11 embodiment of FIGS. 7 and 7A. However, the discussion is applicable to embodiment 11' (FIGS. 8 and 8A) unless expressly stated otherwise. Elements in common between the embodiments of FIGS. 7 and 8 are numbered identically with the addition of the apostrophe to distinguish the two embodiments.

The jacket 11 is dimensioned with respect to a heart H to be treated so when the jacket is applied to the heart, expansion of the heart is constrained to a predetermined limit. The predetermined limit refers to the cardiac expansion limit during diastolic filling of the heart. The limit is typically determined by the physician based on, for example, cardiac output performance or cardiac volume.

The jacket 11 is sized for the heart H to be constrained within the volume 16. The jacket 11 can be slipped about the heart H. The jacket 11 has a length L between the upper and lower ends, 12, 14 sufficient for the jacket 11 to constrain the lower portion LP. The upper end 12 of the jacket 11 extends at least to the valvular annulus VA and further extends to the lower portion LP to constrain at least the lower ventricular extremities LE.

Since enlargement of the lower portion LP is most troublesome, in a preferred embodiment, the jacket 11 is sized so that the upper end 12 can reside in the A–V groove AVG. Where it is desired to constrain enlargement of the upper portion UP, the jacket 10 may be extended to cover the upper portion UP.

Sizing the jacket 11 for the upper end 12 to terminate at the A–V groove AVG is desirable for a number of reasons. First, the groove AVG is a readily identifiable anatomical feature to assist a surgeon in placing the jacket 11. By placing the upper end 12 in the A–V groove AVG, the surgeon is assured the jacket 11 will provide sufficient constraint at the valvular annulus VA. The A–V groove AVG and the major vessels act as natural stops for placement of the jacket 11 while assuring coverage of the valvular annulus VA. Using such features as natural stops is particularly beneficial in minimally invasive surgeries where a surgeon's vision may be obscured or limited.

The jacket 11 need not be directly applied to the epicardium (i.e., outer surface of the myocardium) but can be placed over or under the parietal pericardium.

When the parietal pericardium is opened, the lower portion LP is free of obstructions for applying the jacket 11 over the apex A. If, however, the parietal pericardium is intact, the diaphragmatic attachment to the parietal pericardium inhibits application of the jacket over that portion of the heart which lies directly over the diaphragm. In this situation, the jacket of FIGS. 8 and 8A can be opened along a line extending from the upper end 12' to the lower end 14' of jacket 11'. The jacket can then be applied around the pericardial surface of the heart and the opposing edges of the opened line secured together after placed on the heart. Systems for securing the opposing edges are disclosed in, for example, U.S. Pat. No. 5,702,343, the entire disclosure of which is incorporated herein by reference. The portion of the jacket adjacent to the diaphragm can then be secured to the diaphragm or associated tissues using, for example, sutures, staples, etc.

Figure 8A:
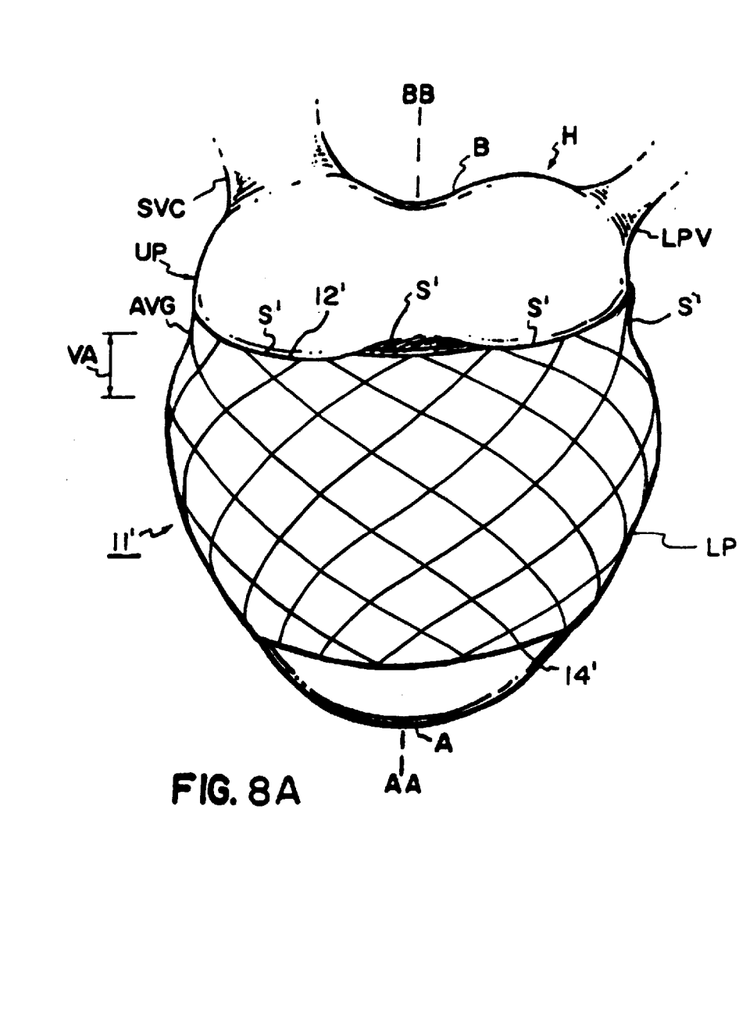
FIG. 8A illustrates a diseased heart in diastole with the device of FIG. 8 applied to the heart.

In the embodiment of FIGS. 7 and 7A, the lower end 14 is closed and the length L is sized for the apex A of the heart H to be received within the lower end 14 when the upper end 12 is placed at the A–V groove AVG. In the embodiment of FIGS. 8 and 8A, the lower end 14' is open and the length L' is sized for the apex A of the heart H to protrude beyond the lower end 14' when the upper end 12' is placed at the A–V groove AVG. The length L' is sized so that the lower end 14' extends beyond the lower ventricular extremities LE such that in both of jackets 11, 11', the myocardium MYO surrounding the ventricles RV, LV is in direct opposition to material of the jacket 11, 10'. Such placement is desirable for the jacket 11, 11' to present a constraint against enlargement of the ventricular walls of the heart H.

After the jacket 11 is positioned on the heart H as described above, the jacket 11 may be secured to the heart by a securing arrangement mounted at the base of the jacket. A suitable securing arrangement includes, for example, a circumferential attachment device, such as a cord, suture, band, adhesive, or shape memory element which passes around the circumference of the base of the jacket. The ends of the attachment device can be fastened together to secure the jacket in place. Alternatively, the base of the jacket can be reinforced for suturing the base of the jacket to the epicardium. The jacket 11 can then be secured to the heart H through sutures or surgical glue, such as, for example, cyanoacrylate glue or fibrin glue.

To permit the jacket 11 to be easily placed on the heart H, the volume and shape of the jacket 11 are larger than the lower portion LP during diastole. So sized, the jacket 11 may be easily slipped around the heart H. Once placed, the jacket's volume and shape are adjusted for the jacket 11 to snugly conform to the external geometry of the heart H during diastole. Such sizing is easily accomplished due to the weave material construction of the jacket 11.

The jacket 11 is adjusted to a snug fit on the heart H during diastole. Care is taken to avoid tightening the jacket 11 too much such that cardiac function is impaired. During diastole, the left ventricle LV fills with blood. If the jacket 11 is too tight, the left ventricle LV cannot adequately expand and left ventricular pressure will rise. During the fitting of the jacket 11, the surgeon can monitor left ventricular pressure. For example, a well-known technique for monitoring so-called pulmonary wedge pressure uses a catheter placed in the pulmonary artery. The wedge pressure provides an indication of filling pressure in the left atrium LA and left ventricle LV. While minor increases in pressure (e.g., 2–3 mm Hg) can be tolerated, the jacket 11 is snugly fit on the heart H but not so tight as to cause a significant increase in left ventricular pressure during diastole.

The biomedical material should constrain cardiac expansion within the predetermined limit during diastolic filling of the heart. Additionally, the biomedical material of the invention can be radioluscent or radiopaque. In one embodiment, the weave material may be made radiopaque by inclusion of radiopaque markers for identification of the outside surface of the heart. As used herein, "radiopaque" means causing the material to be visible on x-ray or fluoroscopic viewing. Suitable radiopaque markers include, for example, platinum wires, titanium wires, and stainless steel wires.

The weave material of this invention has numerous advantages. Such a material is flexible to permit unrestricted movement of the heart H (other than the desired constraint on radial expansion). The material is open defining a plurality of interstitial spaces for fluid permeability. Further, an open material minimizes the amount of surface area of direct contact between the heart H and the material of the jacket, thereby minimizing areas of irritation or abrasion and ultimately minimizing fibrosis and scar tissue.

The open areas of the weave material construction also allow for electrical connection between the heart and surrounding tissue for passage of electrical current to and from the heart. For example, although the weave material is an electrical insulator, the open weave material construction is sufficiently electrically permeable to permit the use of transchest defibrillation of the heart. Also, the open, flexible construction permits other procedures, e.g., coronary bypass, to be performed without removal of the jacket.

The weave material is preferably tear and run resistant. In the event of a material defect or inadvertent tear, such a defect or tear is restricted from propagation by reason of the weave material construction.

A cardiac restraint device comprising a jacket constructed from the weave material of the present invention also can be used to measure cardiac performance. According to this embodiment, the cardiac restraint device is rendered radiopaque by use of a radiographic marker. The radiographic markers are distributed throughout the jacket over the surface of the heart. By evaluation of the markers relative to one another with each heart beat, cardiac performance may be measured. As such, evaluation of cardiac performance may assist in adjusting the predetermined size of the cardiac restraint device.

One advantage of the present invention when the weave material is formed into a jacket is the ability to apply tension to the weave material at certain focal locations that results in approximately equal distribution of the increased tension throughout the entire weave material. When used to constrain a heart to a predetermined size, this feature of the weave material provides for applying a localized tension to the weave material to effect a change in constraint (i.e., decreasing the predetermined limit) throughout the configuration of the weave material. Generally, a cardiac reinforcement device comprising the weave material of the invention may be uniformly adjusted by applying tension to the jacket at a single location. As used herein, "uniformly adjust" means that when tension is applied to the jacket, approximately equal pressure is applied to the heart throughout the surface of the jacket. Thus, a cardiac reinforcement device may be uniformly adjusted by pulling at the apex end of the jacket.

The fabrics and devices of the invention can be applied to the heart via an open thoracotomy or through minimally invasive procedures. Examples of procedures and devices which are suitable for minimally invasive applications of the present invention are described in U.S. Pat. No. 5,702,343.

From the foregoing detailed description and examples, it will be evident that modifications and variations can be made in the products and processes of the invention without departing from the spirit or scope of the invention. Therefore, it is intended that all modifications and variations not departing from the spirit of the invention come within the scope of the claims and their equivalents.

What is claimed is:

1. A cardiac reinforcement device, said device comprising:
   a jacket which can be applied to a heart to constrain cardiac expansion to a predetermined limit; said jacket comprising an apex end and a base end and having a longitudinal axis from said apex end to said base end, said base end of said jacket being oriented toward a base of the heart when said jacket is applied to the heart; and said jacket further comprising:
      a plurality of circumferential rows of cells comprised of a weave material, said rows of cells being approximately perpendicular to said longitudinal axis; wherein said weave material has intersecting strands, said strands being oriented according to:
         spirals emanating in a clockwise direction outward from a common point at said apex end;
         spirals emanating in a counterclockwise direction outward from said common point at said apex end;
         said clockwise spirals and said counterclockwise spirals forming intersections; and
         said intersections forming corners of individual cells;
      each circumferential row of cells comprising an equal number of cells;
      each cell having a cell area;

said cell area being approximately the same for all cells in a selected circumferential row; and at least one circumferential row of cells having cells with said cell area being unequal to said cell area of cells in another circumferential row of cells.

2. The cardiac reinforcement device of claim 1, wherein said cell area of cells in said selected circumferential row of cells is directly correlated with a cross-sectional circumferential dimension of the heart that is surrounded by said selected circumferential row of cells.

3. The cardiac reinforcement device of claim 1, wherein said apex end of said jacket is closed.

4. The cardiac reinforcement device of claim 1, wherein when said device is applied over a plurality of cross-sectional circumferential dimensions from an apex end to a base of the heart, each cross-sectional circumferential dimension of the heart is surrounded by a circumferential row of cells.

5. The cardiac reinforcement device of claim 4, wherein said cell area of cells in said circumferential row of cells is directly correlated with said cross-sectional circumferential dimension of the heart surrounded by said circumferential row of cells.

6. The cardiac reinforcement device of claim 1, wherein said device is uniformly adjustable.

7. The cardiac reinforcement device of claim 1, wherein:
the heart has an upper portion and a lower portion divided by an A–V groove; and
said longitudinal dimension of said jacket is sufficient for said jacket to constrain said lower portion of the heart with said jacket constraining a valvular annulus adjacent said A–V groove and further constraining ventricular lower extremities adjacent said apex end.

8. A method of using a cardiac reinforcement device to constrain heart dilation, said method comprising:
selecting a cardiac reinforcement device, said device comprising a jacket that can be applied to a heart to constrain cardiac expansion to a predetermined limit, said jacket comprising:
an apex end and a base end and having a longitudinal axis from said apex end to said base end, said base end of said jacket is oriented toward a base of the heart when said jacket is applied to the heart;
a plurality of circumferential rows of cells being approximately perpendicular to said longitudinal axis;

each circumferential row comprising an equal number of cell;
each cell having a cell area;
said cell area being approximately the same for all cells in a selected circumferential row; and
at least one circumferential row of cells having cells with said cell area being unequal to said cell area of cells in another circumferential row of cells; wherein said jacket is comprised of a weave material having intersecting strands, wherein said strands are oriented according to:
spirals emanating in a clockwise direction outward from a common point at said apex end;
spirals emanating in a counterclockwise direction outward from said common point at said apex end;
said clockwise spirals and said counterclockwise spirals forming intersections; and
said intersections forming corners of individual cells;
applying said cardiac reinforcement device to the heart; and
adjusting said cardiac reinforcement device to snugly conform to an external geometry of the heart and assume a maximum predetermined size for said jacket to constrain circumferential expansion of the heart beyond a predetermined limit.

9. The method of claim 8, wherein said device is applied over a plurality of cross-sectional circumferential dimensions from an apex to a base of the heart and each cross-sectional circumferential dimension of the heart is surrounded by a circumferential row of cells.

10. The method of claim 9, wherein said cell area of cells in said circumferential row of cells is directly correlated with said cross-sectional circumferential dimension of the heart surrounded by said circumferential row of cells.

11. The method of claim 8, wherein said apex end of said jacket is closed.

12. The method of claim 8, said method further comprising securing said cardiac reinforcement device to the heart.

13. The method of claim 8, wherein said cardiac reinforcement device is uniformly adjustable.

14. The method of claim 13, said method further comprising uniformly adjusting said cardiac reinforcement device by pulling said apex end of said jacket.

* * * * *

UNITED STATES PATENT AND TRADEMARK OFFICE
CERTIFICATE OF CORRECTION

PATENT NO. : 6,241,654 B1  Page 1 of 1
DATED : June 5, 2001
INVENTOR(S) : Clifton A. Alferness It is certified that error appears in the above-identified patent and that said Letters Patent is hereby corrected as shown below:

<u>Title page,</u>
Item [73], delete "Cardiovasculr" and insert -- Cardiovascular --.

Signed and Sealed this

Twenty-ninth Day of June, 2004

JON W. DUDAS
*Acting Director of the United States Patent and Trademark Office*